(12) United States Patent
Berling (10) Patent No.: US 12,339,277 B2
(45) Date of Patent: Jun. 24, 2025

(54) STEPPED MERGED INJECTION FOR SURFACE PLASMON RESONANCE ASSAYS

(71) Applicant: CYTIVA SWEDEN AB, Uppsala (SE)

(72) Inventor: Henrik Berling, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 1098 days.

(21) Appl. No.: 16/329,853

(22) PCT Filed: Aug. 30, 2017

(86) PCT No.: PCT/US2017/049353
§ 371 (c)(1),
(2) Date: Mar. 1, 2019

(87) PCT Pub. No.: WO2018/045017
PCT Pub. Date: Mar. 8, 2018

(65) Prior Publication Data
US 2019/0234943 A1    Aug. 1, 2019

(30) Foreign Application Priority Data

Sep. 1, 2016 (GB) ...................................... 1614773

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/553* (2013.01); *G01N 21/648* (2013.01);
(Continued)

(58) Field of Classification Search
CPC ........... G01N 33/54373; G01N 33/483; G01N 21/553; G01N 21/648; G01N 2001/2893;
(Continued)

(56) References Cited

U.S. PATENT DOCUMENTS 4,794,806 A * 1/1989 Nicoli ...................... G01N 1/38
250/576
6,731,100 B1 * 5/2004 Hansen .................. G01N 33/04
324/637
(Continued)

FOREIGN PATENT DOCUMENTS

EP    1308709    5/2003
JP    2007010439 A    1/2007
(Continued)

OTHER PUBLICATIONS

GB Search Report for corresponding GB application No. 1614773. 8, mailed Jun. 20, 2017; 4 pages.
(Continued)

*Primary Examiner* — Christopher L Chin
(74) *Attorney, Agent, or Firm* — CM Law; Jeff B. Vockrodt (57) ABSTRACT

A device and method for producing data for correction curves for SPR assays provides a plurality of different concentrations of solvent or other compound to the reference surface and active surface of a SPR chip. The concentration are mixed online by two pumps, one connected to a source of a first concentration of solvent or other compound and the other connected to a source of a second, different concentration of solvent or compound. Mixing of the two different concentration of solvent or compound can take place in a fluid mixer and the concentration of solvent or compound in the mixture leaving the fluid mixer can be varied by adjusting the relative speeds of the pumps. The concentration of the solvent or compound mixture can be adjusted during (Continued)

injection of the mixed liquids in order to provide the different concentrations necessary to make a solvent correction curve.

9 Claims, 6 Drawing Sheets

(51) Int. Cl.
  *G01N 21/64* (2006.01)
  *G01N 33/483* (2006.01)
  *G01N 1/28* (2006.01)
  *G01N 21/77* (2006.01)
(52) U.S. Cl.
  CPC ... *G01N 33/483* (2013.01); *G01N 2001/2893* (2013.01); *G01N 2021/7763* (2013.01)
(58) Field of Classification Search
  CPC ... G01N 2021/7763; G01N 2021/6482; G01N 11/02; G01N 1/28; B01L 3/502; B01L 3/5025; B01L 3/502738; B01L 2300/0867; B01L 2400/04; B01L 3/00; G05D 11/02
  USPC ............. 422/82.11; 435/288.5, 288.7, 287.3; 436/52
  See application file for complete search history.

(56) References Cited

U.S. PATENT DOCUMENTS

| | | | |
|---|---|---|---|
| 7,384,604 B2* | 6/2008 | Eaton | ........................ G01N 1/38 |
| | | | 422/417 |
| 2004/0004717 A1 | 1/2004 | Reed | |
| 2007/0004030 A1 | 1/2007 | Ogura et al. | |
| 2013/0157251 A1* | 6/2013 | Quinn | ................. B01F 25/4331 |
| | | | 436/164 |
| 2013/0273564 A1 | 10/2013 | Quinn | |

FOREIGN PATENT DOCUMENTS

| | | |
|---|---|---|
| JP | 2011214862 A | 10/2011 |
| WO | 2011/078777 | 6/2011 |
| WO | 2016/066591 | 5/2016 |
| WO | 2016066591 A1 | 5/2016 |

OTHER PUBLICATIONS

International Search Report and Written Opinion for corresponding PCT application No. PCT/US2017/049353 mailed Dec. 6, 2017; 12 pages.
Office Action received in Japanese Application No. 2019-511894 dated May 24, 2021, with translation, 9 pages.
European Communication pursuant to Article 94(3) EPC dated Apr. 30, 2020, 5 pages.

* cited by examiner

STEPPED MERGED INJECTION FOR SURFACE PLASMON RESONANCE ASSAYS

CROSS REFERENCE

This application is a filing under 35 U.S.C. 371 of international application number PCT/US2017/049353, filed Aug. 30, 2017, which claims priority to Great Britain application number 1614773.8, filed Sep. 1, 2016, the entire disclosure of each of which is hereby incorporated by reference.

BACKGROUND OF THE INVENTION

Surface plasmon resonance assays are a type of assay systems which can monitor molecular interactions in real time, using a noninvasive, label-free technology that responds to changes in the concentration of molecules at a sensor surface as molecules bind to, or dissociate from, the surface. The detection principle is based on surface plasmon resonance (SPR), which is sensitive to changes in refractive index within about 150 nm from the sensor surface. To study the interaction between two binding partners, one partner is attached to the surface and the other is passed over the surface in a continuous flow of sample solution. The SPR response is directly proportional to the change in mass concentration close to the surface.

SPR systems can be used to study interactions involving almost any kind of molecule, from organic drug candidates to proteins, nucleic acids, glycoproteins and even viruses and whole cells. Since the response is a measure of the change in mass concentration, the response per molar unit of interactant is proportional to the molecular weight (smaller molecules give lower molar responses). The detection principle does not require any of the interactants to be labeled, and measurements can be performed on complex mixtures such as cell culture supernatants or cell extracts as well as purified interactants. The identity of the interactant monitored in a complex sample matrix is determined by the interaction specificity of the partner attached to the surface.

Figure 1A:
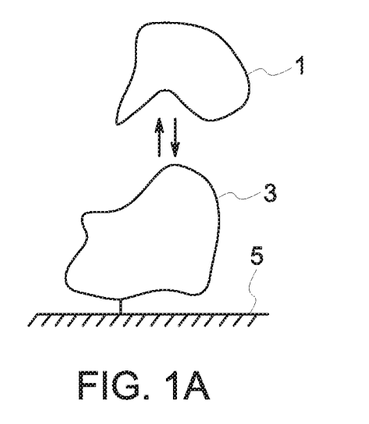
FIG. 1A shows schematically an active surface with a ligand attached directly to it.
Figure 1B:
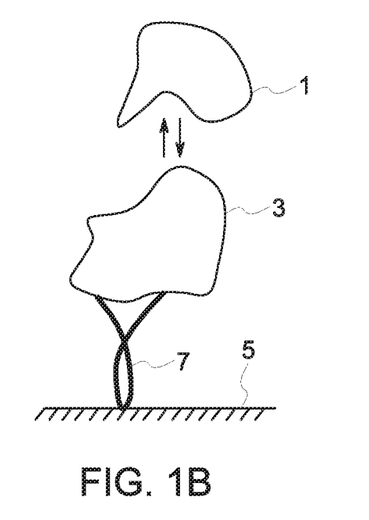
FIG. 1B shows schematically an active surface with a ligand attached indirectly to it via a capturing molecule.
Figure 1C:
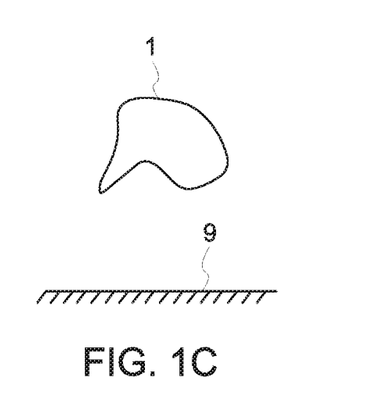
FIG. 1C shows schematically a reference surface without any ligand attached to it.

SPR systems monitor the interaction between two molecules, of which one is attached to the sensor surface (shown by 5 in FIG. 1) and the other is free in solution. The following terms are used in the following in the context of SPR-based assays:

The interaction partner attached (directly or indirectly) to the surface is called the "ligand" (as shown by reference 3 in FIGS. 1a) and 1b)). In drug discovery and development work, the ligand is sometimes referred to as the target molecule. The term "ligand" is applied here in analogy with terminology used in affinity chromatography contexts, and does not imply that the surface-attached molecule is a ligand for a cellular receptor.

The ligand may be attached to the surface either by covalent immobilization using chemical coupling reagents or by capturing through high affinity binding to an immobilized capturing molecule (shown by reference number 7 in FIG. 1b)).

The "analyte" is the interaction partner that is passed in solution over the ligand (as shown by reference number 1 in FIG. 1a)-1c)).

In indirect assay formats the analyte is detected using a secondary detecting molecule, which can bind to both analyte in solution and ligand on the sensor surface. The observed response is derived from binding of detecting molecule to the ligand: the presence of analyte in the sample inhibits this binding so that the response is inversely related to the amount of analyte.

Analysis is performed by injecting sample over the surface in a carefully controlled fashion. The sample is carried in a continuous flow of buffer, termed "running buffer".

Response is measured in resonance units (RU). The response is directly proportional to the concentration of biomolecules on the surface.

Figure 2:
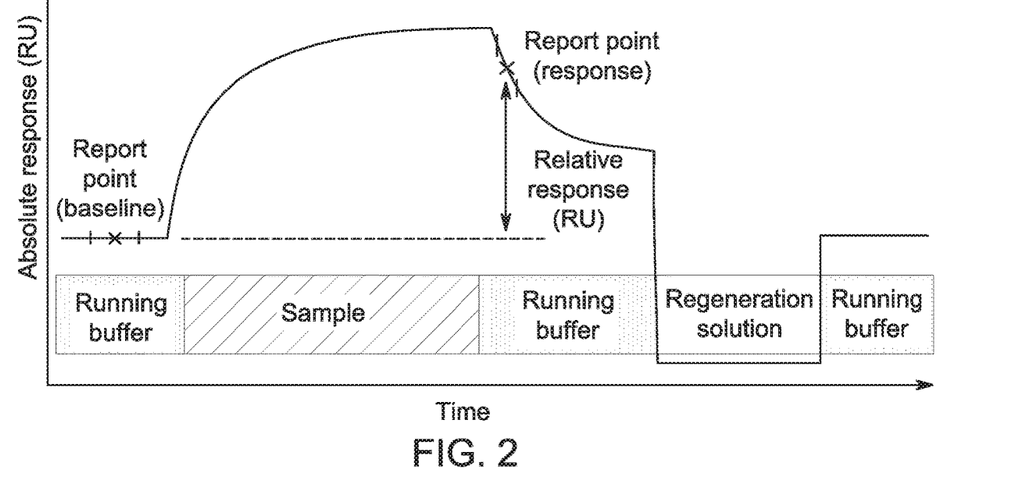
FIG. 2 shows an example of a sensorgram.

A "sensorgram" is a plot of response against time, showing the progress of the interaction (FIG. 2). This curve is displayed directly on the computer screen during the course of an analysis.

A "report point" records the response on a sensorgram at a specific time averaged over a short time window, as well as the slope of the sensorgram over the window. The response may be absolute (above a fixed zero level determined by the detector) or relative to the response at another specified report point (FIG. 2).

"Regeneration" is the process of removing bound analyte from the surface after an analysis cycle without damaging the ligand, in preparation for a new cycle.

SPR detection monitors changes in refractive index close to the surface, and differences in refractive index between running buffer and injected sample will be recorded as a rapid shift in response at the beginning and end of the injection. This is referred to as a "bulk refractive index effect" or "bulk shift".

The response in a SPR system is directly related to the change in mass concentration on the surface, so that molar responses (i.e. responses for a given number of molecules) are proportional to the size of the molecule involved. A given response will represent a higher molar concentration of a small molecule than a large one: conversely, a given number of molecules binding to the surface will give a lower response if the molecule is small. The relationship between response and surface concentration is essentially constant for proteins regardless of amino acid composition and sequence, and is similar for most other biological macromolecules.

The "sensor chip" in SPR systems may consist of a glass slide coated with a thin layer of gold. These components, together with the docking system for mounting the sensor chip in an optical system, are required for generation of an SPR signal. To provide a suitable environment for the molecular interactions being studied, the gold surface is covered by a linker layer and (on most sensor chip types) a matrix of modified dextran. It is the surface matrix that determines the properties of the sensor chip with respect to ligand attachment and molecular interaction. A chip comprises an active surface (shown by reference number 5 in FIGS. 1a) and 1b)) with ligands and a reference surface (shown by reference number 9 in FIG. 1c)) without ligands or with ligands which are similar to the ligands on the active surface but which do not bind with the analyte. Accordingly, the reference surface does not respond to the presence of the molecules which react with the ligand on the active surface. The signals from the reference surface give a control response against which the signals representing the response from the active surface can be compared.

In general, SPR systems are compatible with most buffer substances used in biological studies. However, many low molecular weight organic compounds, relevant particularly in pharmaceutical development work, are sparingly soluble in aqueous buffers and require addition of organic solvents. Dimethyl sulfoxide (DMSO) is commonly used. Typically SPR systems can be used with buffers containing up to 10%

DMSO. However, organic solvents contribute significantly to the bulk refractive index of samples and buffers: 1% DMSO contributes approximately 1200 RU to the response level. Expected responses from low molecular weight analytes, which often need organic solvents to maintain solubility, may be as low as 10-20 RU or less. It is therefore crucial that the measured responses are accurately compensated for any variations in organic solvent concentration. The procedures for adjusting measured sample responses for the effects of varying concentrations of solvent effects are called solvent correction.

These procedures are especially relevant for work with small organic analytes that require inclusion of organic solvents (commonly dimethyl sulfoxide, DMSO) in the buffer to maintain analyte solubility.

Figure 3:
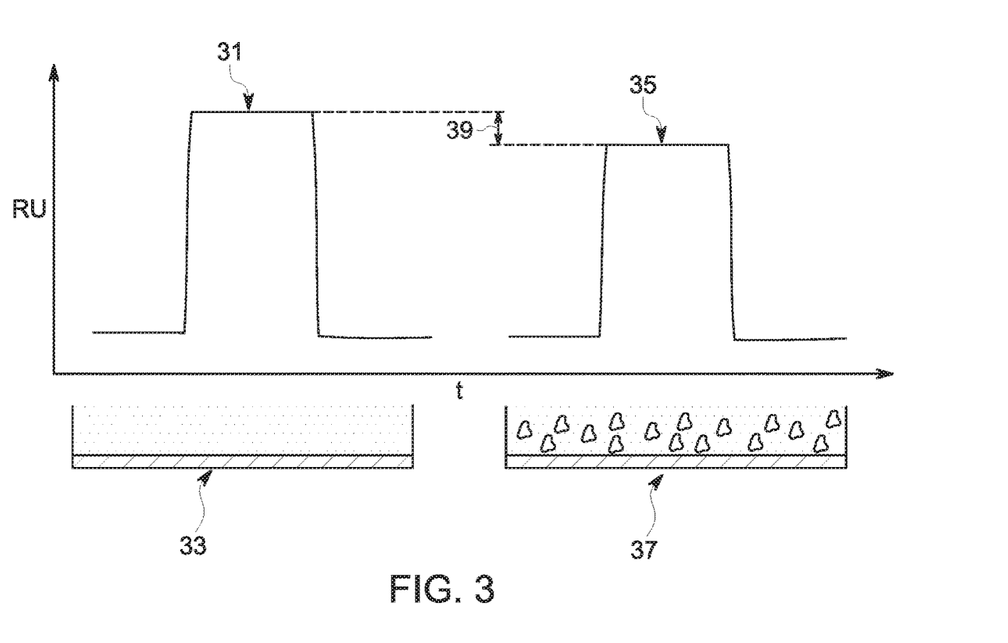
FIG. 3 shows schematically the difference between the response on a reference surface and a response on an active surface.

Simple subtraction of a reference response is not sufficiently accurate for these purposes when differences in bulk shifts between samples can be of the same order of magnitude as (or larger than) the expected response from analyte binding. One reason for this is that the volume of solution accessible to the sample will differ on the reference and active surfaces unless the two surfaces have the same attached protein concentration. As a result of the volume excluded by ligand molecules, the bulk shift will be smaller on the active surface than the reference surface (as shown in a plot of response (RU) vs time (t) in FIG. 3) where reference numeral 31 represents the response on the reference surface (33), reference numeral 35 represents the response on the active surface (37) and reference numeral 39 represents the difference in response due to the excluded volume response on the reference surface.

There are other factors in addition to excluded volume involved in solvent correction that are outside the scope of this discussion, so that solvent correction is essentially an empirical procedure.

Solvent correction is necessary under a combination of three circumstances, commonly met in work with low molecular weight analytes such as drug candidates:
the expected analyte responses are low,
the ligand is a macromolecule immobilized at a high density on the surface,
the bulk response is high in relation to the measured binding response.

In drug discovery and development work, the analytes are often small molecules which give correspondingly low response values (typically of the order of 10-50 RU or less). High levels of immobilized ligands (several thousand RU) are used to maximize the analyte response, enhancing the excluded volume effect described above. Samples generally include DMSO to maintain solubility, resulting in high bulk responses. A difference of 1% (percentage points) in DMSO concentration corresponds to a difference of about 1200 RU in response, so that small variations in DMSO concentration, unavoidable in the preparation of diverse samples, easily lead to variations in bulk response of the same order of magnitude as the expected sample responses.

Figure 4:
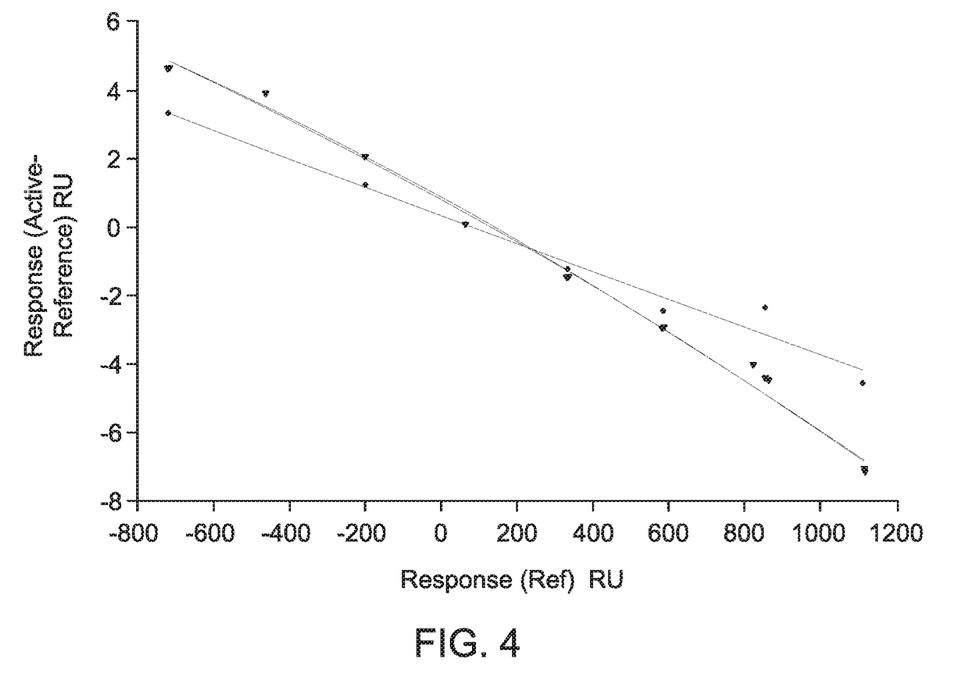
FIG. 4 shows a correction curve containing plots of responses obtained when different concentrations of an organic solution are provided over a pair of active and reference surfaces in a sensor chip.
Figure 5:
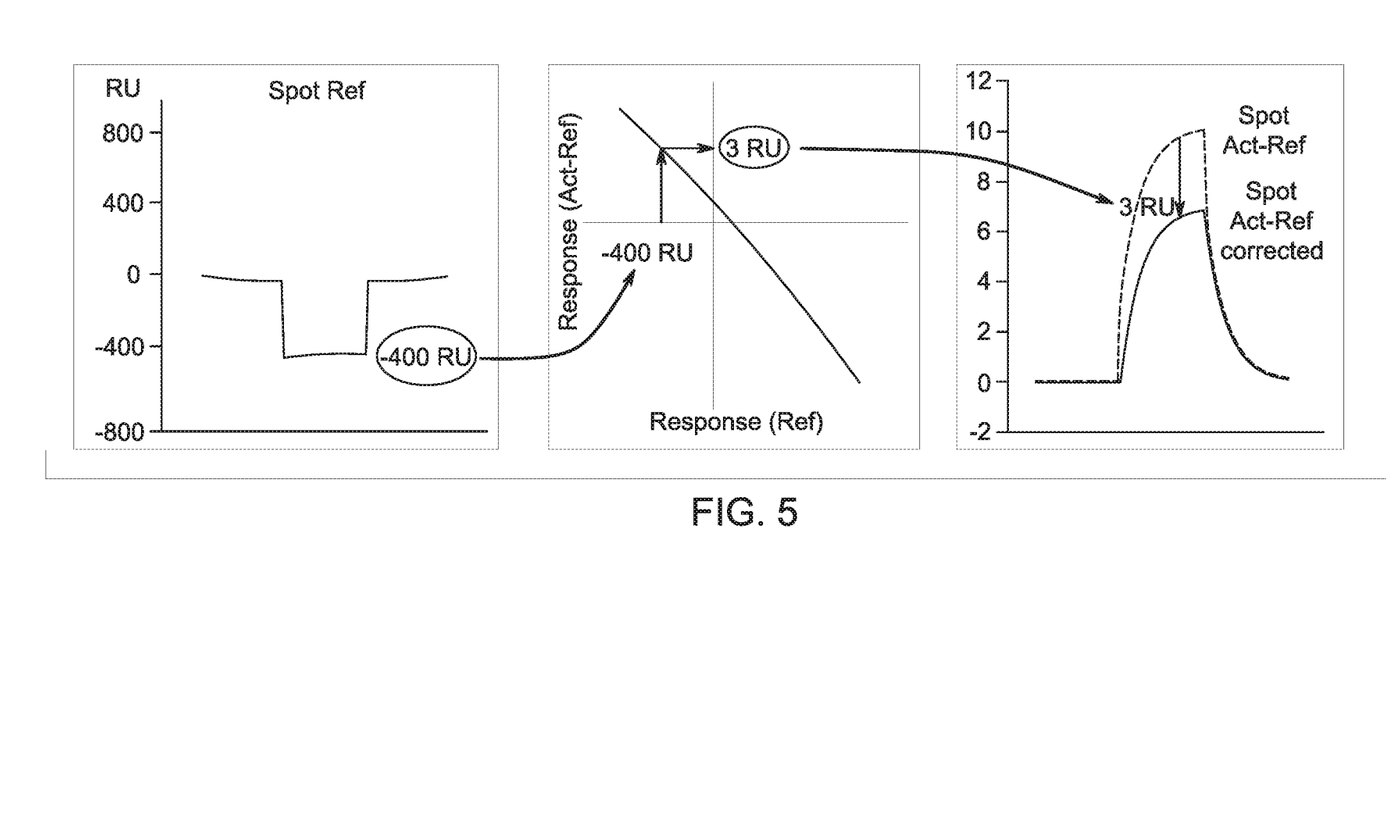
FIG. 5 shows how a correction curve is applied to the response obtained during an assay.

Solvent correction values are determined by preparing a range of DMSO concentrations, for example eight different concentrations, performing eight different injections in which each injection comprises the step of injecting blank samples each containing a different one of the different concentrations of DMSO over the reference surface and active surface, and plotting the reference-subtracted response from the active surface against the relative response from the reference surface. This creates a calibration curve, referred to as the solvent correction curve, for the solvent effect as a function of the reference response—an example of a correction curve is shown in FIG. 4. The production and use of a correction curve is well known in the art and thus will not be described in detail. The correction curve can be used to adjust each sample measurement be compensate for the solvent effect on the basis of the response on the reference surface (see FIG. 5).

One problem with current methods of preparing solvent correction curves is that a solvent correction curve has to be prepared for every pair of reference surface and active surface—which is time consuming. The time spent connecting the individual concentrations to the system between each injection of a different concentration of DMSO is wasted and the whole procedure is time-consuming and prone to errors. For example, pipetting errors which may occur in the preparation of the different concentrations of DMSO may add significant errors to the solvent correction curve. DMSO is hydroscopic and prolonged storage of the prepared concentrations of DMSO in open containers will lead to changes in the concentration of DMSO and subsequently errors in the calibration curves.

Additionally, it is important to strive for exactly the same DMSO concentration in samples and running buffer and to minimize variations in DMSO content between samples. In order to achieve this when preparing samples for assays where solvent correction is necessary it has normally been necessary to:
Use carefully designed buffer preparation and sample dilution protocols to ensure consistent DMSO concentrations. Samples that are stored in DMSO should be diluted in such a way as to give the same final DMSO concentration as in the running buffer.
Cover the sample plates with foil directly after preparation to avoid changes in DMSO concentration resulting from evaporation and absorption of water from the air as DMSO is hygroscopic. Such preparations are time-consuming and costly.

BRIEF DESCRIPTION OF THE INVENTION

At least some of problems of the prior art can be overcome by providing a mixing system for online mixing of only two different solutions containing different amounts of organic solvent (e.g. DMSO) or other compound in different proportions. The mixing system can comprise one pump for pumping a first concentration of organic solvent in buffer solution (e.g. 1% by volume of organic solvent) from a first bulk supply and one pump for pumping a second concentration of organic solvent in buffer solution (e.g. 10% by volume of organic solvent) from a second bulk supply. The pumps can pump the fluids to a fluid mixer where they are mixed thoroughly. By changing the relative flow rates of the pumps it is possible to achieve different concentrations of organic solvent in the liquid leaving the mixing region. For example, if the flow rate of the first concentration of organic solvent is x ml/minute and the flow rate of the second concentration of organic solvent is zero then the concentration leaving the fluid mixer will be 1%. If the flow rate of the first concentration of organic solvent is x/2 ml/minute and the flow rate of the second concentration of organic solvent is also x/2 ml/minute then the concentration leaving the fluid mixer will be 5.5%. If the flow rate of the first concentration of organic solvent is zero ml/minute and the flow rate of the second concentration of organic solvent is x ml/minute then the concentration leaving the fluid mixer will be 10%. The mixed liquid can be then injected over the active surface and reference surface and the responses detected.

As the concentration of organic solvent can be changed almost instantaneously by changing the relative flow rate of the pumps, time is saved in the procedure. Furthermore, the operator has to only prepare the two bulk supplies (i.e. the two bulk supplies containing the different concentrations of buffer solution and organic solvent) instead of eight different concentrations of organic solvent and the buffer solution. The correction curve can then be made by performing one injection with, for example eight steps, each comprising a different concentration of organic solvent formed during the injection, instead of performing eight different injections with eight different previously prepared concentrations of organic solvent.

DETAILED DESCRIPTION OF THE INVENTION

Figure 6:
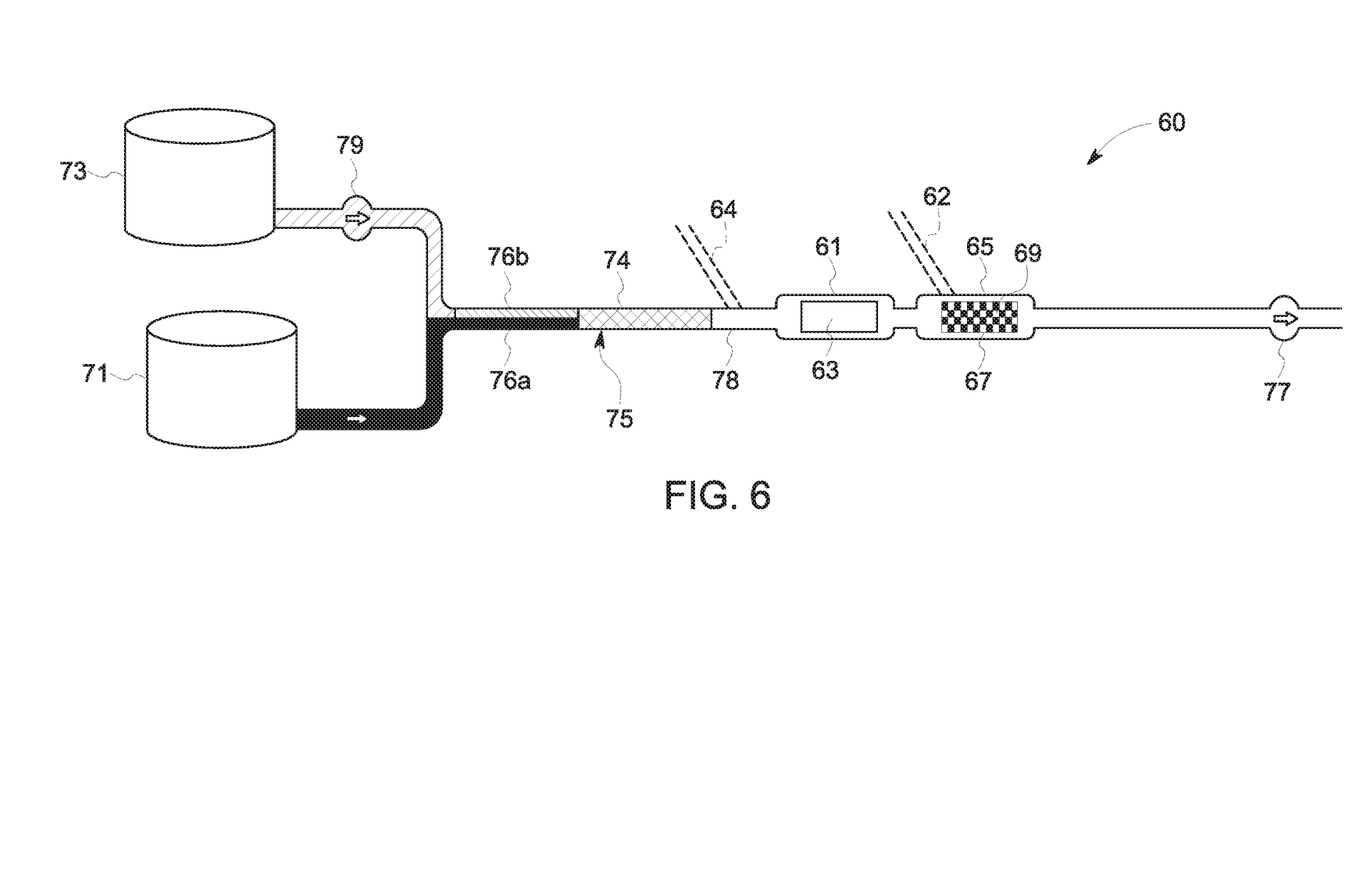
FIG. 6 shows schematically a fluid mixer circuit for performing the present invention.

FIG. 6 shows schematically a simplified embodiment of a device (60) for producing different concentration of a solvent, for example an organic solvent such as DMSO, suitable for producing correction curves for an assay device, in particular an SPR assay device. Some of the features known from the prior art which are necessary for preparing the device for use, for example a ligand inlet (62) leading to the active surface to provide it with ligands, and/or which are necessary to run the device, for example a running buffer inlet (64) for providing running buffer to the device are shown in dashed lines, while for the sake of ease of comprehension of the figure the necessary valves, pumps and control system are omitted. The assay device comprises flow cell (61) with a reference surface (63) and a second flow cell (65) with an active surface (67) wherein the active surface comprises a quantity of ligands (69) and the reference surface comprises a lesser quantity or no ligands. In this embodiment of the invention the flow cells are in series with the reference surface (63) upstream of the active surface (67) but in another embodiment of the present invention the surfaces are arranged in series with the active surface upstream of the reference surface. In a further embodiment of the present invention the two surfaces are arranged in parallel.

In each embodiment of the present invention the flow cells are in liquid communication with a first source (71) of a liquid comprising a first concentration (×1) of a solvent (e.g. DMSO) or other compound and a second source (73) of a liquid comprising a second concentration (×2) of the same solvent or the same other compound. For the sake of brevity in the following the invention will be illustrated by an example in which the solvent or compound is DMSO but it possible to replace the DMSO with any other compound. Preferably one concentration of the solvent for example the first concentration (×1) is the lowest concentration of solvent (or compound) which is to be used, for example 1% DMSO by volume, and the second concentration (×2) is the highest concentration of solvent which is to be used, for example 10% DMSO by volume.

A fluid mixer (75) is arranged in the pathway between the supplies of liquid and the flow cells. The fluid mixer has at least two inlets (76a, 76b), a first inlet (76a) connectable to the first source and a second inlet (76b) connectable to the second source. The fluid mixer has at least one outlet (78) for mixed liquids connectable to the flow cells. The fluid mixer is adapted to ensure that the liquids are mixed before leaving the fluid mixer by the outlet or outlets for mixed liquids (78). The fluid mixer may be in the form of or comprise a mixer chamber and/or a mixer pathway (74) arranged to cause mixing of the two liquids for example by provision of stirring means or example by generating turbulent flow. The resulting mixed fluid can subsequently be injected across each of the active and reference surfaces.

A first pump (77) is provided downstream of the flow cells for drawing fluid from the fluid mixer (75) across the flow cells. A second pump (79) is provided to pump fluid from the second source of a liquid to the mixing chamber via the second inlet (76b). When the first pump is activated to provide a flow of x ml/minute and the second pump is switched off then only fluid from the first source will be able to flow through the fluid mixer to the flow cells and it will do so at the flow rate, determined by the first pump i.e. x ml/minute. In a similar way, when the first pump is activated to provide a flow of x ml/minute and the second pump is activated to provide the same flow rate of x ml/minute then only fluid from the second source will flow through the fluid mixer to the flow cells.

Thus, it is possible to provide any concentration of solvent between ×1 and ×2 by varying the relative speeds of the first and second pumps. For example if the speed of the first pump is maintained constant then increasing the speed of the second pump will lead to an increase in the concentration of solvent in the fluid leaving the fluid mixer because the flow of less concentrated solvent from the first source will diminish as the flow of more concentrated solvent from the second source increases. Such an arrangement provides a simple way of controlling the proportions of the liquids entering the fluid mixer while maintain a constant liquid flow rate through the mixer.

In an alternative embodiment of the invention, not shown, there are two pumps but both of these are upstream of the mixing chamber. A first pump connects the first source of a liquid to the first inlet of the mixing chamber and a second pump connects the second source of a liquid to the second inlet of the mixing chamber. The proportion of each liquid flowing into the mixing chamber will therefore be proportional to the flow rate of each of the pumps.

Figure 7:
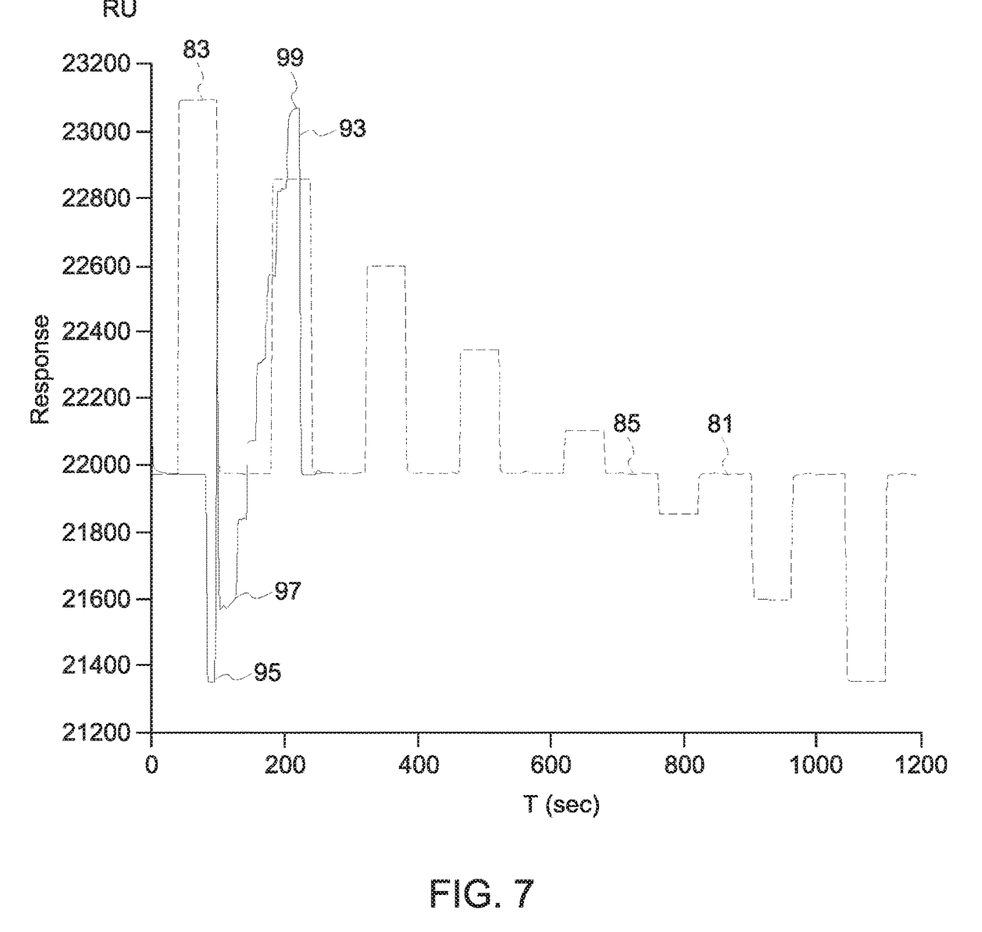
FIG. 7 shows a comparison between a run for obtaining data for a correction curve in accordance with the prior art and a run for obtaining data for a correction curve in accordance with a method according to the present invention.

FIG. 7 shows a sensorgram with a comparison between a run for collecting data for using in preparing a correction curve according to a prior art method, and a run for collecting data suitable for producing a correction curve performed using a method according to the present invention wherein the run is performed on a reference cell and an active cell in a device of the type shown in FIG. 6.

In order to make a clearer comparison between the runs in the figure, the prior art type run was performed with the highest concentration of DMSO (shown by reference numeral 83) at the beginning while in the run according to the present invention the lowest concentration of DMSO was used at the beginning (as shown by reference number 95). In the first run (shown by curve 81) which was performed according to the prior art method, 8 solutions containing different concentrations of DMSO were prepared. These were connected in turn to the flow channel leading to the inlet of a flow cell with a reference surface and a flow cell with an active surface. Each solution was allowed to flow until a steady response had been achieved and recorded before being disconnected and the next solution connected and injected into the flow cells. Running buffer was injected into the flow cells between each injection of a DMSO-containing liquid as shown for example by reference numeral 85). Thus there was no mixing of the 8 different solutions containing DMSO. In this example in which the supplies of the different liquids had to be attached and detached manually the total time for providing the eight readings for a correction curve was around 1100 seconds, i.e. over 18 minutes.

In the second run (shown by curve 93) for producing data for producing a correction curve performed according to a method of the present invention, a first solution comprising the lowest concentration (×1) of the solvent (or compound) intended to be used in an assay was prepared and a vessel containing this first solution was connected to the first inlet (76a) of the mixer. A second solution comprising the highest concentration (×2) of the solvent (or compound) intended to be used in the assay was prepared and a vessel containing this second solution was connected to the second (76b) inlet of the fluid mixer (75).

The pump (77) downstream of the flow cells was activated and the second pump (79) was switched off. This caused a flow of only the solution containing the lowest concentration of the solvent to flow through said fluid inlet into the fluid mixer and subsequently through the outlet of the fluid mixer to the active surface and the reference surface (shown at reference numeral 95) and the corresponding step in the response curves was recorded. The second pump was then activated at a low flow rate while maintaining the flow rate of the first pump. This allowed a flow of the second concentration of the solvent to said fluid mixer (as shown at 97) while reducing the flow rate of the first concentration to the fluid mixer, thereby achieving a new mixed concentration of the solvent leaving the fluid mixer and travelling over the reference and active surfaces. The responses from the reference and active surfaces to this new concentration were recorded. The flow rate of the second pump was increased and a reading of the response to the new concentration of solvent was made. This procedure was repeated until the flow rates of the first and second pumps were the same whereby only the second solution with the highest concentration of solvent was injected into the flow cells as shown at 99. As can be seen from the figure, this process took around 230 seconds and thus was significantly quicker than the manual injections. This method allows multiple different concentration of a solvent or compound to be quickly prepared and subsequently injected into the assay device.

There is no limitation on the number of different concentrations of the solvent or compound which can be produces using a device and method according to the present invention. Preferably the number of concentration used is equal to 8, as is commonly used in the prior art. However, as the method and device according to the invention allows correction curves to be produced more quickly than in the prior art, in order to give more precision to the correction curve, it could be preferable to record the response of a greater number of different concentrations of solvent or compound, for example a total of 16 concentrations or even 32 different concentrations. As each concentration can be quickly mixed and injected, the method and device of the present invention allows the operator to choose between producing data for a correction curve with the same precision as the prior art (i.e. eight data points) in a much shorter time, or to produce more data (i.e. data relating to more concentrations of solvent or compound e.g. 16 or 32 different concentrations) in order to get greater precision while still saving time.

The above description of the present disclosure is provided for the purpose of illustration, and it would be understood by those skilled in the art that various changes and modifications may be made without changing the concept and essential features of the present disclosure. Thus, it is clear that the above-described embodiments are illustrative in all aspects and do not limit the present disclosure. It shall be understood that all modifications and embodiments conceived from the meaning and scope of the claims and their equivalents are included in the scope of the present disclosure.

I claim:

1. A fluid circuit for a surface plasmon resonance (SPR) device, the fluid circuit comprising:
   a first flow cell of the SPR device, the first flow cell having a reference surface;
   a second flow cell of the SPR device, the second flow cell having an active surface, wherein the active surface comprises a quantity of ligands and the reference surface comprises a lesser quantity or no ligands;
   a first pump and a second pump;
   a first liquid source;
   a second liquid source, the second liquid source upstream of the second pump; and,
   a mixer having a first inlet and a second inlet; the second inlet being positioned downstream of the second pump and the first inlet being positioned downstream of the first liquid source, there being no pump between the first liquid source and the first inlet; the mixer having an outlet that is positioned upstream of the first flow cell, the second flow cell and the first pump, the first pump being positioned downstream of the first flow cell and the second flow cell.

2. The fluid circuit of claim 1, wherein the first flow cell and the second flow cell are arranged in series.

3. The fluid circuit of claim 2, wherein the first flow cell is downstream of the mixer, and the second flow cell is downstream of the first flow cell.

4. The fluid circuit of claim 1, further comprising a buffer inlet connected to the first flow cell and a ligand inlet connected to the second flow cell.

5. The fluid circuit of claim 1, wherein the first liquid source comprises a first liquid at a first concentration, and the second liquid source comprises the first liquid at a second concentration.

6. The fluid circuit of claim 5, where the first liquid is dimethyl sulfoxide (DMSO).

7. The fluid circuit of claim 1, wherein during operation of the SPR device, the fluid circuit is capable of controlling a proportion of the first liquid and the second liquid entering the fluid mixer while maintaining a constant liquid flow rate through the mixer.

8. The fluid circuit of claim 7, wherein the proportion of the first liquid and the second liquid entering the fluid mixer is changed by altering the flow rate of the second pump and without altering the flow rate of the first pump.

9. The fluid circuit of claim 1, wherein during operation, when the first pump is activated to provide a first flow rate and the second pump is switched off, then only fluid from the first source will be able to flow through the fluid mixer to the flow cells and it will do so at the first flow rate.

\* \* \* \* \*